US 6,790,969 B2

(12) United States Patent
Müller et al.

(10) Patent No.: US 6,790,969 B2
(45) Date of Patent: Sep. 14, 2004

(54) METHOD FOR REGENERATING A ZEOLITE CATALYST

(75) Inventors: Ulrich Müller, Neustadt (DE); Joaquim Henrique Teles, Otterstadt (DE); Anne Wenzel, Eggenstein-Leopoldshafen (DE); Wolfgang Harder, Weinheim (DE); Peter Rudolf, Ladenburg (DE); Alwin Rehfinger, Mutterstadt (DE); Peter Baβler, Viernheim (DE); Norbert Rieber, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/363,407

(22) PCT Filed: Sep. 11, 2001

(86) PCT No.: PCT/EP01/10489

§ 371 (c)(1), (2), (4) Date: Mar. 4, 2003

(87) PCT Pub. No.: WO02/22260

PCT Pub. Date: Mar. 21, 2002

(65) Prior Publication Data

US 2003/0181738 A1 Sep. 25, 2003

(30) Foreign Application Priority Data

Sep. 11, 2000 (DE) .......................................... 100 44 788

(51) Int. Cl.$^7$ ...................... C07D 301/12; C07D 301/19
(52) U.S. Cl. ........................ 549/531; 549/529; 549/541
(58) Field of Search ................................. 549/531, 529, 549/541

(56) References Cited

U.S. PATENT DOCUMENTS 5,912,367 A * 6/1999 Chang ........................ 549/529

FOREIGN PATENT DOCUMENTS

| DE | 195 28 220 | 1/1997 |
| DE | 197 23 950 | 12/1998 |
| EP | 0 085 234 | 8/1983 |
| WO | 98 00413 | 1/1998 |
| WO | 98/18555 | 5/1998 |
| WO | 98/55228 | 12/1998 |

* cited by examiner

Primary Examiner—Ba K. Trinh
(74) Attorney, Agent, or Firm—Oblon, Spivak, McClelland, Maier & Neustadt, P.C.

(57) ABSTRACT

A process for regenerating a zeolite catalyst comprises thermal treatment of the catalyst at above 120° C. in the presence of a gas stream comprising hydrogen.

27 Claims, No Drawings

METHOD FOR REGENERATING A ZEOLITE CATALYST

BACKGROUND OF THE INVENTION

1. Field of the Invention

The present invention relates to a process for regenerating a zeolite catalyst and to an integrated process for preparing an epoxide in which the regeneration according to the present invention is carried out.

2. Description of the Background

It is known from the prior art that the catalytic activity of heterogeneous catalysts for the oxidation of organic compounds in the liquid phase, in particular the epoxidation of organic compounds having at least one C—C double bond using a hydroperoxide in the presence of a zeolite catalyst, decreases as the run time increases and the corresponding catalysts then have to be regenerated.

Accordingly, processes for regenerating zeolite catalysts are already known from the prior art. On this subject, reference may be made to WO 98/55228 and the prior art cited therein. In this prior art, essentially two different procedures for catalyst regeneration are proposed.

1. If the catalyst is used in suspension, it is firstly separated from the liquid reaction product and transferred to a regeneration apparatus suitable for the regeneration and is regenerated there by thermal treatment in the presence of oxygen;
2. If the catalyst is used as a fixed bed, the liquid phase is drained or pumped out and the catalyst is regenerated by thermal treatment in the absence of oxygen either in the reactor itself or in a separate regeneration apparatus.

Furthermore, regeneration by treatment of the catalyst with a liquid which is an oxidizing agent, e.g. hydrogen peroxide, at elevated temperature has been described a number of times, for example in DE-A 195 28 220 and WO 98/18555.

SUMMARY OF THE INVENTION

It is an object of the present invention to provide a further improved, in particular more effective, process for the regeneration of zeolite catalysts, which can be integrated without problems into continuous and integrated processes for preparing epoxides of the type under discussion here and which leads to opening or changeover of the reactors without long shutdown times and downtimes. In particular, this process should be suitable for regenerating zeolite catalysts which are used in an oxidation in the fixed-bed mode. The regeneration process of the present invention should especially substantially prevent or at least greatly reduce the formation of a hot spot in a catalyst bed during regeneration, since such local overheating of the catalyst has an adverse effect on the activity or mechanical stability of the catalyst when it is subsequently reused in the integrated process of the present invention for the oxidation of an alkene.

DETAILED DESCRIPTION OF THE PREFERRED EMBODIMENTS

We have found that this object is achieved by the process of the present invention for regenerating a zeolite catalyst.

The present invention accordingly provides a process for regenerating a zeolite catalyst, which comprises thermal treatment of the catalyst at above 120° C. in the presence of a gas stream comprising hydrogen.

The regeneration time is preferably chosen so that the catalyst regains at least 85% of its original activity.

In the process of the present invention, it is possible to regenerate either catalysts in powder form as are used in suspension or catalysts in the form of shaped bodies, e.g. extrudates, packed in a fixed bed, or catalysts crystallized on meshes, e.g. stainless steel or Kanthal, or packing or coated catalysts comprising an inner core of $SiO_2$, $\alpha\text{-}Al_2O_3$, strongly calcined $TiO_2$ or steatite and an active catalyst shell comprising a zeolite.

If the catalyst has been used in the suspension mode, it firstly has to be separated from the reaction solution by a separation step, e.g. filtration or centrifugation. The at least partially deactivated pulverulent catalyst obtained in this way can then be regenerated. The steps carried out at elevated temperatures during the regeneration process are preferably carried out in rotary tube furnaces in the case of such pulverulent catalysts. In the regeneration of a catalyst which is used in the suspension mode, particular preference is given, for the purposes of coupling the reaction in the suspension mode and the regeneration process of the present invention, to removing part of the at least partially deactivated catalyst continuously from the reaction, regenerating it externally by means of the process of the present invention and reintroducing the regenerated catalyst into the reaction in the suspension mode.

Apart from the regeneration of catalysts in powder form, the process of the present invention can also be employed for regenerating catalysts in the form of shaped bodies, for example those packed in a fixed bed. In the regeneration of a catalyst packed in a fixed bed, the regeneration is preferably carried out in the reaction apparatus itself without the catalyst having to be removed and reinstalled, so that it is subjected to no additional mechanical stress. In the regeneration of the catalyst in the reaction apparatus itself, the reaction is firstly interrupted, any reaction mixture present is removed, the regeneration is carried out and the reaction is subsequently continued.

The regeneration of the present invention proceeds essentially identically in both the regeneration of pulverulent catalysts and the regeneration of catalysts in shaped form.

The process of the present invention is particularly suitable for regeneration in a fixed-bed reactor, especially a tube reactor or a shell-and-tube reactor. The terms "tube reactor" and "shell-and-tube reactor" refer to parallel assemblies of many channels in the form of tubes, where the tubes can have any cross section. The tubes are fixed in space relative to one another, preferably have a spacing between them and are preferably surrounded by a jacket (shell) which encloses all the tubes. In this way, for example, a heating or cooling medium can be passed through the shell so that all tubes are uniformly heated/cooled.

Furthermore, the individual tubes within the tube reactor or shell-and-tube reactor which is preferably employed have a length of preferably from about 0.5 to 15 m, more preferably from 5 to 15 m and in particular from about 8 to 12 m.

The catalyst preferably remains in the reactor during regeneration. The process of the present invention can also be employed for regenerating zeolite catalysts located in a plurality of reactors connected in parallel or in series or (at least partly) in parallel and in series.

The regeneration of the present invention is carried out at above 120° C., preferably above 350° C. and in particular at from 400° C. to 650° C.

The regeneration gases used are in principle subject to no restrictions as long as the regeneration can be carried out so that the catalyst in the interior of the reactor does not become so hot as a result of, for example, combustion of the organic deposits present thereon that the pore structure of the catalyst and/or the reactor is/are damaged, the formation of explosive gas mixtures is prevented and the regeneration gas comprises hydrogen. The regeneration is preferably carried out so that a hot spot at which the temperature is increased by from 10 to 20° C., preferably not more than 20° C., is formed within the catalyst bed.

In a particularly preferred embodiment, the regeneration gas comprises carbon dioxide or hydrogen or carbon dioxide and hydrogen, in each case possibly in combination with CO. The content of $CO_2$ and/or hydrogen during the regeneration is from 0.1 to 100% by volume, preferably from 0.5 to 20% by volume and more preferably from 1 to 5% by volume.

The regeneration gas may further comprise other inert gases, e.g. nitrogen, noble gases such as argon or helium, hydrocarbons such as methane or ethane and natural gas.

The zeolite catalysts regenerated in the present process are subject to no particular restrictions.

Zeolites are, as is known, crystalline aluminosilicates having ordered channel and cage structures in which micropores, preferably smaller than about 0.9 nm, are present. The framework of such zeolites is built up of $SiO_4$ and $AlO_4$ tetrahedra joined via common oxygen bridges. An overview of the known structures may be found, for example, in W. M. Meier, D. H. Olson and Ch. Baerlocher, "Atlas of Zeolite Structure Types", Elsevier, 4$^{th}$ Edition, London 1996.

Zeolites in which no aluminum is present and the Si(IV) of the silicate lattice has been partly replaced by titanium as Ti(IV) are also known. These titanium zeolites, in particular those having a crystal structure of the MFI type, and possible ways of preparing them are described, for example, in EP-A 0 311 983 or EP-A 405 978. Apart from silicon and titanium, such materials may further comprise additional elements such as aluminum, zirconium, tin, iron, cobalt, nickel, gallium, boron or small amounts of fluorine. In the zeolite catalysts which are preferably regenerated using the process of the present invention, part or all of the titanium of the zeolite can be replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, WO 98/03394, WO 98/03395, EP-A 0 311 983 or EP-A 0 405 978, whose relevant contents are hereby fully incorporated by reference into the present application.

It is known that titanium zeolites having an MFI structure can be identified by means of a particular X-ray diffraction pattern and also by means of lattice vibration bands in the infrared region (IR) at about 960 cm$^{-1}$, and are thus distinguished from alkali metal titanates or crystalline and amorphous $TiO_2$ phases.

Specific examples are titanium-, germanium-, tellurium-, vanadium-, chromium-, niobium- and zirconium-containing zeolites having a pentasil zeolite structure, in particular the types assigned X-ray crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG and ZON structures and to mixed structures made up of two or more of the abovementioned structures. Further zeolites which can be used in the process of the present invention are titanium-containing zeolites having the ITQ-4, SSZ-24, ™-1, UTD-1, CIT-1 or CIT-5 structure. Further titanium-containing zeolites which may be mentioned are those of the ZSM-48 or ZSM-12 structure.

In the process of the present invention, particular preference is given to Ti zeolites having an MFI, MEL or mixed MFI/MEL structure. Specific examples of further preferred Ti zeolites are the Ti-containing zeolite catalysts which are generally referred to as "TS-1", "TS-2", "TS-3" and also Ti zeolites having a lattice structure isomorphous with β-zeolite.

Accordingly, the present invention also provides a process as described above in which the catalyst is a titanium silicalite of the structure TS-1.

For the purposes of the present invention, the term "alkene" refers to all compounds having at least one C—C double bond.

As examples of such organic compounds having at least one C—C double bond, mention may be made of the following alkenes:

ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, and saturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

In the process of the present invention, preference is given to using alkenes having from 2 to 8 carbon atoms. Particular preference is given to reacting ethene, propene and butene, very particularly preferably propene.

Accordingly, the present invention also provides a process as described above or an integrated process as described above in which the alkene is propene.

For the purposes of the present invention, the term "hydroperoxide" encompasses all hydroperoxides including hydrogen peroxide. Details of hydroperoxide solutions which can be used in the process of the present invention and their preparation may be found in the prior art. Reference may be made, for example, to DE 19723950.1 and the prior art cited therein.

The hydrogen peroxide used can be prepared, for example, by means of the anthraquinone process by which virtually all hydrogen peroxide is produced. This process is based on the catalytic hydrogenation of an anthraquinone compound to form the corresponding anthrahydroquinone compound, subsequent reaction of this with oxygen to form hydrogen peroxide and subsequent extraction of the hydrogen peroxide formed. The catalysis cycle is closed by renewed hydrogenation of the anthraquinone compound obtained back.

An overview of the anthraquinone process is given in "Ullmann's Encyclopedia of Industrial Chemistry", $5^{th}$ Edition, Volume 13, pages 447 to 456.

Hydrogen peroxide can also be obtained by anodic oxidation of sulfuric acid to form peroxodisulfuric acid with simultaneous evolution of hydrogen at the cathode. Hydrolysis of the peroxodisulfuric acid then leads via peroxosulfuric acid to hydrogen peroxide and sulfuric acid, which is thus recovered.

It is of course also possible to prepare hydrogen peroxide from the elements.

Before the use of hydrogen peroxide in the process of the invention, it is possible to free, for example, a commercially available hydrogen peroxide solution of undesirable ions. Conceivable methods are, inter alia, those described in, for example, WO 98/54086, DE-A 42 22 109 or WO 92/06918. It is likewise possible to remove at least one salt present in the hydrogen peroxide solution from this solution by means of ion exchange in an apparatus having at least one nonacidic ion exchange bed having a cross-sectional area A and a height H such that H is smaller than or equal to $2.5 \times A^{1/2}$, in particular less than or equal to $1.5 \times A^{1/2}$. For the purposes of the present invention, it is in principle possible to use all nonacidic ion exchange beds comprising cation exchangers and/or anion exchangers. It is also possible to use both cation and anion exchangers within an ion exchange bed to give a mixed bed. In a preferred embodiment of the present invention, only one type of nonionic ion exchanger is used. Further preference is given to using a basic ion exchanger, particularly preferably a basic anion exchanger and more particularly preferably a weakly basic anion exchanger.

In a particularly preferred embodiment, the present invention provides a process for regenerating a zeolite catalyst, which comprises the steps (1) to (4) below:

(1) washing the zeolite catalyst with a solvent (2) drying the washed zeolite catalyst at from −50 to 250° C.

(3) heating the dried catalyst (4) regenerating the heated catalyst by means of a process according to the present invention.

This preferred regeneration process particularly preferably further comprises the additional steps (5) and/or (6):

(5) cooling the regenerated catalyst obtained in step (4)

(6) conditioning the catalyst obtained in step (4) or in step (5).

These steps will now once again be described in detail. It should be noted at the beginning that the zeolite catalyst to be regenerated is generally a catalyst which is used in an oxidation of an alkene by reaction of the alkene with a hydroperoxide, preferably a reaction carried out continuously, and now has to be regenerated as a result of a drop in activity. As indicated above, the regeneration of the present invention is preferably carried out in the reactor or reactors in which the reaction of the alkene with a hydroperoxide in the presence of the catalyst to be regenerated is also carried out.

In a further, very particularly preferred embodiment, the reactor is operated as part of an integrated system including the work-up of the desired product and the regeneration according to the present invention, since this mode of operation allows a closed solvent circuit.

(1) Washing of the Zeolite Catalyst with a Solvent

The first step of this embodiment of the regeneration of the present invention comprises firstly washing the deactivated catalyst with a solvent. For this purpose, the introduction of the feedstocks, namely hydroperoxide and organic compound, is firstly interrupted. As solvent, it is possible to use any solvent in which the respective reaction product of the oxidation of the alkene dissolves readily. Preference is given to using such solvents selected from the group consisting of water, alcohols, preferably methanol, aldehydes, acids, e.g. formic acid, acetic acid and propionic acid, nitrites, hydrocarbons, halogenated hydrocarbons. For details of such solvents, reference may be made to WO 98/55228, whose relevant contents are fully incorporated by reference into the present application.

Preference is given to using solvents which are already functioning as solvents in the reaction, e.g. the epoxidation of olefins using the catalyst to be regenerated. Examples of such solvents used in the epoxidation of olefins are: water, alcohols, e.g. methanol, ethanol, 1-propanol, 2-propanol, 2-methyl-2-propanol, 1-butanol, 2-butanol, allyl alcohol and ethylene glycol, or ketones such as acetone, 2-butanone, 2-methyl-3-butanone, 2-pentanone, 3-pentanone, 2-methyl-4-pentanone and cyclohexanone.

If the solvent already being used in the reaction is employed as solvent for washing, its introduction is continued and the catalyst is washed with the solvent at generally from 40 to 200° C., if desired with increasing temperature and under superatmospheric pressure. Washing is preferably continued until the content of reaction product in the washings drops to below 1% of the initial value. If a different solvent is to be used, the introduction of hydroperoxide, the feedstock and the solvent of the reaction is interrupted after the reaction and the introduction of solvent for washing is commenced. Particular preference is given to using the same solvent for the reaction and for washing the catalyst.

The duration of the washing procedure is subject to no restrictions, although relatively long washing times and thus very substantial removal of the reaction product or the organic deposits are advantageous.

(2) Drying of the Washed Zeolite Catalyst at from −50 to 250° C.

After the catalyst has been washed, the solvent used is drained or pumped from the reactor. The porous catalyst then still contains considerable amounts of adhering solvent which is mostly removed by drying in a gas stream at from −50 to 250° C., with the temperature used being in the vicinity of the boiling point of the solvent at the respective pressure. The temperature is typically in the range from 50° C. below to 50° C. above the boiling point.

An inert gas, e.g. nitrogen, argon, $CO_2$, hydrogen, synthesis gas, methane, ethane or natural gas, is generally used for drying. Preference is given to using nitrogen. The solvent-laden gas is then either disposed of, for example by burning in a flare, or is fed at a suitable point to, for example, the work-up of the reaction product of the process for the oxidation of an alkane and the solvent present therein is recovered.

In a preferred embodiment, washing is carried out under superatmospheric pressure at a temperature above the boiling point of the solvent and, after draining off the solvent, the pressure is reduced to such an extent that part of the solvent is vaporized by the latent heat of the reactor before or during the introduction of gas for drying.

To supply heat during this step, it is possible to use either a gas or a liquid, for example within the shell of a tube reactor. Preference is given to using a liquid for the temperature range below 150° C. and a gas for the temperature range above 150° C.

(3) Heating of the Dried Catalyst

After drying, the catalyst to be regenerated is heated. This heating can be carried out by all methods known to those skilled in the art, with heating preferably being carried out in the presence of a stream of inert gas such as nitrogen, $CO_2$, argon, methane, ethane or natural gas.

In a particularly preferred embodiment of the process of the present invention, the catalyst is located in the tubes of a shell-and-tube reactor. In such reactors, the heat is introduced into the system via the space within the shell. The heating rate has to be selected so that no unacceptably high mechanical stresses occur in the reactor. Typical heating rates are from 0.01° C./min to 0.2° C./min.

(4) Regeneration of the Heated Catalyst by Means of a Process According to the Present Invention The regeneration of the catalyst, as described in detail in the present application, is subsequently carried out.

(5) Cooling of the Regenerated Catalyst Obtained in Step (4)

After completion of the regeneration in step (4), the regenerated catalyst, preferably the entire reactor with the regenerated catalyst present therein, can be cooled to preferably below 200° C.

(6) Conditioning of the Catalyst Obtained in Step (4) or Step (5)

After regeneration according to the present invention or after cooling, the catalyst can be additionally conditioned to remove the heat of sorption of the solvent or the starting materials in a controlled manner before reuse of the catalyst. For this purpose, small amounts of a solvent, preferably the same solvent which has been used for the reaction or for washing the catalyst, in particular an alcohol such as methanol, are mixed into the inert gas flowing past the catalyst and the inert gas stream laden with solvent vapor is passed through the catalyst bed. The solvent content and the volume flow of the conditioning gas are selected so that no unacceptable peak temperature occurs in the catalyst. The temperature increase is preferably not more than 100° C. above the mean temperature of the heat transfer medium, e.g. in the space within the shell of a tube reactor.

After the liberation of heat has abated, the supply of conditioning gas with solvent is interrupted and the reactor, preferably the fixed-bed reactor, is filled with liquid and operation is recommenced.

In the optional steps (5) and (6) of the process of the present invention, it is important that both cooling and conditioning are not carried out too quickly since in both cases the catalyst bed in the reactor can be adversely affected. Furthermore, an excessively rapid temperature rise within the catalyst during conditioning should be avoided for the same reasons.

The regenerated catalyst is preferably, as indicated above, reused for the reaction of the alkene with the hydroperoxide. In particular, the regeneration of the present invention or the integrated process for the oxidation of an alkene can be employed for the conversion of propylene into propylene oxide by means of hydrogen peroxide, more preferably in methanolic solution.

The process of the present invention has, in particular, the following advantages:

the gentle reaction conditions make it possible to regenerate zeolite catalysts in such a way that the activity is largely retained after regeneration;

the regeneration process of the present invention can, when using a fixed-bed catalyst, be carried out in the reactor itself without the catalyst being removed;

the solvents used in the regeneration process of the present invention can be identical to the solvents present during the reaction and can all be fully circulated.

The invention is illustrated by the examples below.

EXAMPLES

Example 1

A heterogeneous catalyst (60% by weight of titanium zeolite TS-1, 40% by weight of $SiO_2$ binder) used in the epoxidation of propene to propylene oxide was removed from a fixed-bed tube reactor after a running time of several hundred hours (850 h). According to chemical analysis, the material had a carbon content of 1.2% by weight. In a standard activity test as described in DE 19859561.1, example 10, this catalyst gave a propylene oxide content of only 3.6% by weight.

In a tube reactor (length: 2000 mm, internal diameter: 40 mm), 800 g of this material were heated for 2 hours in a stream of 900 1/h of nitrogen and 100 1/h of $CO_2$, maintained under these conditions for 6 hours and cooled again. No evolution of heat in the reactor was observed.

The regenerated catalyst had a carbon content of only 0.3% by weight. In the above-defined standard activity test, this catalyst gave a propylene oxide content of 4.4% by weight.

Example 2

A heterogeneous catalyst (60% by weight of titanium zeolite TS-1, 40% by weight of $SiO_2$ binder) used in the epoxidation of propene to propylene oxide was removed from a fixed-bed tube reactor after a running time of several hundred hours (850 h). According to chemical analysis, the material had a carbon content of 1.2% by weight. In the above-defined standard activity test, this catalyst gave a propylene oxide content of only 3.6% by weight.

In a tube reactor (length: 200 mm, internal diameter: 50 mm), 30 g of this material were heated at 600° C. for 2 hours in a stream of 90 1/h of nitrogen and 10 1/h of $CO_2$, maintained under these conditions for 6 hours and cooled again.

The regenerated catalyst had a carbon content of only 0.1% by weight. In the above-defined standard activity test, this catalyst gave a propylene oxide content of 4.3% by weight.

Example 3

A heterogeneous catalyst (60% by weight of titanium zeolite TS-1, 40% by weight of $SiO_2$ binder) used in the epoxidation of propene to propylene oxide was removed from a fixed-bed tube reactor after a running time of several hundred hours (850 h). According to chemical analysis, the material had a carbon content of 1.2% by weight. In the above-defined standard activity test, this catalyst gave a propylene oxide content of only 3.6% by weight.

In a tube reactor (length: 2000 mm, internal diameter: 40 mm), 800 g of this material were heated at 450° C. for 2 hours in a stream of 900 l/h of nitrogen and 100 l/h of $CO_2$, maintained under these conditions for 6 hours and cooled again. No evolution of heat in the reactor was observed.

The regenerated catalyst had a carbon content of only 0.1% by weight. In the above-defined standard activity test, this catalyst gave a propylene oxide content of 4.9% by weight.

We claim:

1. A process for the oxidation of an alkene, which comprises reaction of the alkene with a hydroperoxide in the presence of a zeolite catalyst and subsequent regeneration of the catalyst by means of a process for regenerating a zeolite catalyst, said process for regenerating comprising:
   (1) washing the zeolite catalyst with a solvent;
   (2) drying the washed zeolite catalyst at a temperature ranging from −50 to 250° C.;
   (3) heating the dried catalyst; and
   (4) thermally treating the catalyst at a temperature above 120° C. in the presence of a gas stream comprising hydrogen.

2. A process as claimed in claim 1, wherein the gas stream further comprises $CO_2$ and/or CO in addition to hydrogen.

3. A process as claimed in claim 1, wherein the zeolite catalyst is a titanium silicalite having an MFI structure.

4. A process as claimed in claim 1, wherein the regeneration is conducted in a fixed-bed reactor.

5. A process as claimed in claim 4, wherein the fixed-bed reactor is a tube reactor or a shell-and-tube reactor.

6. A process as claimed in claim 1 which further comprises at least one of steps (5) and (6) below, which are conducted after step (4):
   (5) cooling the regenerated catalyst obtained in step (4); and
   (6) conditioning the catalyst obtained in step (4) or in step (5),
   wherein small amounts of solvent are mixed into the inert gas flowing past the catalyst and the inert gas stream laden with solvent vapor is passed through the catalyst bed.

7. A process as claimed in claim 1, wherein the regenerated catalyst is reused for the reaction of the alkene with the hydroperoxide.

8. A process as claimed in claim 7, wherein the alkene is propene and the hydroperoxide is hydrogen peroxide.

9. A process for the oxidation of an alkene, which comprises reaction of the alkene with a hydroperoxide in the presence of a zeolite catalyst which is a titanium silicalite having an MFI structure, and subsequent regeneration of the catalyst by means of a process for regenerating a zeolite catalyst, said process for regenerating comprising:
   (1) washing the zeolite catalyst with a solvent;
   (2) drying the washed zeolite catalyst at a temperature ranging from −50 to 250° C.;
   (3) heating the dried catalyst; and
   (4) thermally treating the catalyst at a temperature above 120° C. in the presence of a gas stream comprising hydrogen, wherein the regenerated catalyst is reused for the reaction of the alkene with the hydroperoxide.

10. A process as claimed in claim 9, wherein the gas stream further comprises $CO_2$ and/or CO in addition to hydrogen.

11. A process as claimed in claim 9, wherein the regeneration is conducted in a fixed-bed reactor, said fixed-bed reactor being a tube reactor or a shell-and-tube reactor.

12. A process as claimed in claim 9, which further comprises at least one of steps (5) and (6) below, which are conducted after step (4):
   (5) cooling the regenerated catalyst obtained in step (4); and
   (6) conditioning the catalyst obtained in step (4) or in step (5),
   wherein small amounts of solvent are mixed into the inert gas flowing past the catalyst and the inert gas stream laden with solvent vapor is passed through the catalyst bed.

13. A process as claimed in claim 9, wherein the alkene is propene and the hydroperoxide is hydrogen peroxide.

14. A process for the oxidation of propene with hydrogen peroxide, which comprises reaction of the propene with a hydrogen peroxide in the presence of a solvent and in the presence of a zeolite catalyst which is a titanium silicalite having an MFI structure, and subsequent regeneration of the catalyst by means of a process for regenerating a zeolite catalyst, said process for regenerating comprising:
   (1) washing the zeolite catalyst with the solvent used in the reaction of the propene with hydrogen peroxide;
   (2) drying the washed zeolite catalyst at a temperature ranging from −50 to 250° C.;
   (3) heating the dried catalyst; and
   (4) thermally treating the catalyst at a temperature above 120° C. in the presence of a gas stream comprising hydrogen.

15. A process as claimed in claim 14, wherein the gas stream further comprises $CO_2$ and/or CO in addition to hydrogen.

16. A process as claimed in claim 14, wherein the regeneration is conducted in a fixed-bed reactor, said fixed-bed reactor being a tube reactor or a shell-and-tube reactor.

17. A process as claimed in claim 14, wherein the regenerated catalyst is reused for the reaction of propene with the hydrogen peroxide.

18. A process for the oxidation of an alkene with a hydroperoxide, which comprises reaction of the alkene with the hydroperoxide in the presence of a solvent and in the presence of a zeolite catalyst which is a titanium silicalite having an MFI structure, and subsequent regeneration of the catalyst by means of a process for regenerating a zeolite catalyst, said regeneration being conducted in a fixed-bed reactor, and said process for regenerating comprising:
   (1) washing the zeolite catalyst with the solvent used in the reaction of the alkene with hydrogen peroxide;
   (2) drying the washed zeolite catalyst at a temperature ranging from −50 to 250° C.;
   (3) heating the dried catalyst;
   (4) thermally treating the catalyst at a temperature above 120° C. in the presence of a gas stream comprising hydrogen;
   (5) cooling the regenerated catalyst obtained in step (4); and
   (6) conditioning the catalyst obtained in step (4) or in step (5), wherein small amounts of solvent are mixed into the inert gas flowing past the catalyst and the inert gas stream laden with solvent vapor is passed through the catalyst bed, where said solvent that is mixed into the inert gas that flows past the catalyst is the solvent which is used in the reaction of the alkene with hydrogen peroxide and which is used for washing the zeolite catalyst in (1).

19. A process as claimed in claim 18, wherein the alkene is propene, the hydroperoxide is hydrogen peroxide, and the solvent is methanol.

20. A process as claimed in claim 1, wherein the heating step (3) is conducted in the stream of an inert gas at a heating rate ranging from 0.01° C./min to 0.2° C./min.

21. A process as claimed in claim 1, wherein the heating step (3) is conducted in the stream of an inert gas at a heating rate ranging from 0.01° C./min to 0.2° C./min.

22. A process as claimed in claim 14, wherein the heating step (3) is conducted in the stream of an inert gas at a heating rate ranging from 0.01° C./min to 0.2° C./min.

23. A process as claimed in claim 18, wherein the heating step (3) is conducted in the stream of an inert gas at a heating rate ranging from 0.01° C./min to 0.2° C./min.

24. A process as claimed in claim 20, wherein the heating is conducted in an inert atmosphere selected from the group consisting of nitrogen, $CO_2$, argon, methane, ethane or natural gas.

25. A process as claimed in claim 21, wherein the heating is conducted in an inert atmosphere selected from the group consisting of nitrogen, $CO_2$, argon, methane, ethane or natural gas.

26. A process as claimed in claim 22, wherein the heating is conducted in an inert atmosphere selected from the group consisting of nitrogen, $CO_2$, argon, methane, ethane or natural gas.

27. A process as claimed in claim 23, wherein the heating is conducted in an inert atmosphere selected from the group consisting of nitrogen, $CO_2$, argon, methane, ethane or natural gas.

* * * * *

UNITED STATES PATENT AND TRADEMARK OFFICE
CERTIFICATE OF CORRECTION

PATENT NO. : 6,790,969 B2
DATED : September 14, 2004
INVENTOR(S) : Ulrich Müller et al.

It is certified that error appears in the above-identified patent and that said Letters Patent is hereby corrected as shown below:

Column 9,
Line 15, "driving the washed zeolite" should read -- drying the washed zeolite --.

Signed and Sealed this

First Day of November, 2005

JON W. DUDAS
*Director of the United States Patent and Trademark Office*